(12) United States Patent
Banholzer et al.

(10) Patent No.: US 8,686,148 B2
(45) Date of Patent: *Apr. 1, 2014

(54) PROCESS FOR PREPARING NEW TIOTROPIUM SALTS, NEW TIOTROPIUM SALTS AS SUCH AND PHARMACEUTICAL COMPOSITIONS THEREOF

(75) Inventors: Rolf Banholzer, Stuttgart (DE); Waldemar Pfrengle, Biberach (DE); Peter Sieger, Mittelbiberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 937 days.

This patent is subject to a terminal disclaimer.

(21) Appl. No.: 10/977,753

(22) Filed: Oct. 29, 2004

(65) Prior Publication Data

US 2005/0131007 A1    Jun. 16, 2005

Related U.S. Application Data

(60) Provisional application No. 60/528,339, filed on Dec. 10, 2003.

(30) Foreign Application Priority Data

Nov. 3, 2003    (EP) .................................... 03025075

(51) Int. Cl.
    C07D 491/08    (2006.01)
(52) U.S. Cl.
    USPC .............................................. 546/91; 546/80
(58) Field of Classification Search
    USPC ........................................................... 546/91
    See application file for complete search history.

(56) References Cited

U.S. PATENT DOCUMENTS

| | | | |
|---|---|---|---|
| 2,597,329 A | 5/1952 | Howe et al. | |
| 3,551,492 A * | 12/1970 | Mizzoni | 564/354 |
| 5,610,163 A | 3/1997 | Banholzer et al. | |
| 6,486,321 B2 * | 11/2002 | Banholzer et al. | 546/89 |
| 6,506,900 B1 * | 1/2003 | Banholzer et al. | 546/91 |
| 6,608,055 B2 * | 8/2003 | Sieger et al. | 514/229.8 |
| 6,747,154 B2 * | 6/2004 | Brandenburg et al. | 546/91 |
| 6,777,423 B2 * | 8/2004 | Banholzer et al. | 514/291 |
| 6,908,055 B2 | 6/2005 | Hoelsaeter et al. | |
| 6,908,928 B2 * | 6/2005 | Banholzer et al. | 514/291 |
| 2002/0110529 A1 | 8/2002 | Bechtold-Peters et al. | |
| 2002/0111363 A1 | 8/2002 | Drechsel et al. | |
| 2002/0133010 A1 | 9/2002 | Banholzer et al. | |
| 2002/0137764 A1 | 9/2002 | Drechsel et al. | |
| 2002/0183292 A1 | 12/2002 | Pairet et al. | |
| 2002/0193392 A1 | 12/2002 | Schmelzer et al. | |
| 2002/0193394 A1 | 12/2002 | Disse | |
| 2003/0070679 A1 | 4/2003 | Hochrainer | |
| 2003/0130300 A1 | 7/2003 | Linz et al. | |
| 2003/0171586 A1 | 9/2003 | Banholzer et al. | |
| 2003/0181478 A1 | 9/2003 | Drechsel et al. | |
| 2003/0235538 A1 | 12/2003 | Zierenberg | |
| 2004/0024007 A1 | 2/2004 | Pairet et al. | |
| 2004/0030040 A1 | 2/2004 | Schmid et al. | |
| 2004/0039011 A1 | 2/2004 | Disse et al. | |
| 2004/0176338 A1 | 9/2004 | Pairet et al. | |
| 2005/0038252 A1 * | 2/2005 | Morschhaeuser et al. | 546/91 |
| 2005/0084457 A1 | 4/2005 | Hochrainer et al. | |
| 2005/0096341 A1 | 5/2005 | Banholzer et al. | |
| 2005/0131007 A1 | 6/2005 | Banholzer et al. | |
| 2005/0143410 A1 * | 6/2005 | Pfrengle et al. | 514/291 |
| 2006/0039868 A1 | 2/2006 | Bechtold-Peters et al. | |
| 2006/0047120 A1 * | 3/2006 | Lock et al. | 546/91 |
| 2006/0251586 A1 | 11/2006 | Zierenberg | |
| 2006/0287530 A1 | 12/2006 | Pop et al. | |
| 2007/0104655 A1 | 5/2007 | Zierenberg et al. | |
| 2007/0110678 A1 | 5/2007 | Zierenberg et al. | |
| 2008/0236579 A1 | 10/2008 | Zierenberg et al. | |
| 2008/0292563 A1 | 11/2008 | Bechtold-Peters et al. | |
| 2009/0137621 A1 | 5/2009 | Hochrainer et al. | |

FOREIGN PATENT DOCUMENTS

| | | |
|---|---|---|
| DE | 101 11 843 A1 | 9/2002 |
| EP | 0 418 716 A1 | 3/1991 |
| JP | 61-065885 | 4/1986 |
| JP | 11-152286 | 6/1999 |
| JP | 2002 193925 | 7/2002 |
| WO | WO-02/30928 | 4/2002 |
| WO | WO 02/36104 A2 | 5/2002 |
| WO | WO 02/38154 A1 | 5/2002 |
| WO | WO-02/48238 | 6/2002 |
| WO | WO 02/051840 A1 | 7/2002 |
| WO | WO-03/068233 | 8/2003 |
| WO | WO-03/068234 | 8/2003 |
| WO | WO-03/084502 | 10/2003 |
| WO | WO-03/084509 | 10/2003 |
| WO | WO-03/084519 | 10/2003 |
| WO | WO-2005 042528 | 5/2005 |

OTHER PUBLICATIONS

Essential of Ion Exchange, Francis De'Silva, 1999.*
West, Anthony R., Solid State Chemistry and its Applications, Wiley, New York, 1988, pp. 358 & 365.*
Wikepedia definition of Ion Exchange .—2008.*
Ion Exchange resin 2008, David Alchin.*
Chemistry Reactivity,Kotz and Treichel 4th edition, pp. 880 and 881., 1999.*
Ono Pharmaceutical Co., Ltd., "Hydrochloric acid salt of phenylalkanoic acid ester, and its production," Patent Abstracts of Japan, Publication Date: Jun. 8, 1999; English Abstract of JP11-152286.
Thomson Innovation, English Translation of Claims and Description Retrieved From Patent Record View on Aug. 4, 2010; English Abstract of WO-02/30928.
Thomson Innovation, English Translation of Claims and Description Retrieved From Patent Record View on Aug. 4, 2010; English Abstract of WO-02/48238.
Wako Pure Chem Ind Ltd, "Sulfonium Salt Compound," Patent Abstracts of Japan, Publication Date: Jul. 10, 2002; English Abstract of JP2002-193925.

(Continued)

Primary Examiner — Rita Desai
(74) Attorney, Agent, or Firm — Michael P. Morris; Wendy A. Petka (57) ABSTRACT

The invention relates to a process for preparing new tiotropium salts, these new tiotropium salts as such, pharmaceutical formulations containing them and their use for preparing a medicament for the treatment of respiratory complaints, particularly for the treatment of COPD (chronic obstructive pulmonary disease) and asthma.

2 Claims, 3 Drawing Sheets

(56) References Cited

OTHER PUBLICATIONS

Thomson Innovation, English Translation of Claims and Description Retrieved From Patent Record View on Aug. 4, 2010; English Abstract of WO-03/084519.

Tanabe Seiyaku Co., "Novel Synthetic Intermediate and Production," Data Supplied from the esp@cenet database—Worldwide, Publication Date: Apr. 4, 1986; English Abstract for JP61-065885.
English Abstract for EP 0 418 716 A1, Mar. 27, 1991.
English Abstract for DE 101 11 843 A1, Sep. 19, 2002.

* cited by examiner

Figure 1:
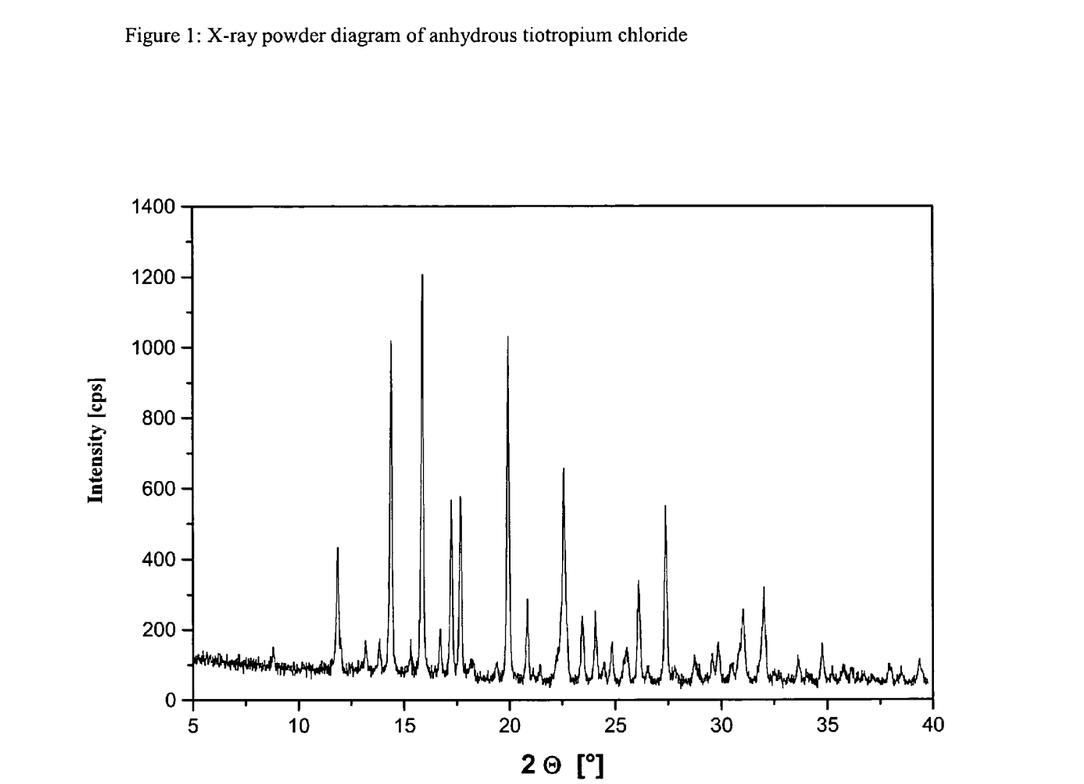

Figure 1: X-ray powder diagram of anhydrous tiotropium chloride

Figure 2:
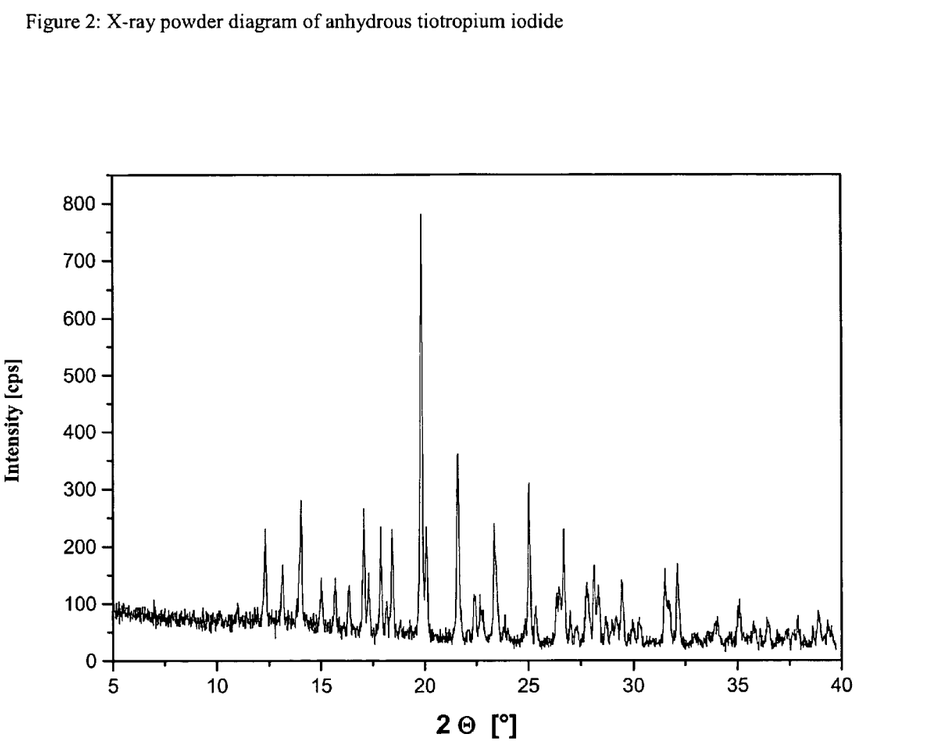

Figure 2: X-ray powder diagram of anhydrous tiotropium iodide

Figure 3:

PROCESS FOR PREPARING NEW TIOTROPIUM SALTS, NEW TIOTROPIUM SALTS AS SUCH AND PHARMACEUTICAL COMPOSITIONS THEREOF

RELATED APPLICATIONS

Benefit of U.S. Provisional Application Ser. No. 60/528,339, filed on Dec. 10, 2003, is hereby claimed, and which application is incorporated herein in its entirety.

FIELD OF THE INVENTION

The invention relates to a process for preparing new tiotropium salts, these new tiotropium salts as such, pharmaceutical formulations containing them and their use for preparing a medicament for the treatment of respiratory complaints, particularly for the treatment of COPD (chronic obstructive pulmonary disease) and asthma.

BACKGROUND TO THE INVENTION

Tiotropium bromide is known from European Patent Application EP 418 716 A1 and has the following chemical structure:

Tiotropium bromide is a highly effective anticholinergic with a long-lasting effect, which may be used to treat respiratory complaints, particularly COPD (chronic obstructive pulmonary disease) and asthma. By tiotropium is meant the free ammonium cation.

Hitherto, there has been no explicit description in the prior art of salts of tiotropium other than the bromide. The halides and also the alkyl- and arylsulphonate of tiotropium should also be obtainable analogously using the method described in EP 418 716 (cf. Diagram 1). However, other salts of tiotropium cannot be produced using this method.

The aim of the present invention is to provide an alternative method of synthesis for preparing tiotropium salts which enables other tiotropium salts to be synthesised by a simple, non-aggressive method which is universally applicable.

DETAILED DESCRIPTION OF THE INVENTION

The problem stated above is solved by the process according to the invention as described hereinafter.

The invention relates to a process for preparing new tiotropium salts of formula 1 wherein $X^-$ denotes an anion,
characterised in that a tiotropium salt of formula 2 wherein
$Y^-$ denotes an anion different from $X^-$ selected from the group consisting of halide, $C_1$-$C_{10}$-alkylsulphonate, $C_1$-$C_{10}$-alkylsulphate, $C_6$-$C_{10}$-arylsulphonate,
is reacted in a suitable solvent with an ion source Kat-X wherein Kat denotes a cation and X may have the meanings given above.

In the process according to the invention the compounds Kat-X are used as the source for the anions $X^-$. These are salts which contain a cation (Kat) in addition to the anion $X^-$. Theoretically, all the salts Kat-X, wherein X may have the meanings given above, may be used for the reaction according to the invention. However, salts Kat-X wherein Kat denotes a cation selected from the series of the alkali or alkaline earth metals are preferred. In addition, it is also preferable according to the invention to use salts wherein Kat denotes ammonium ($NH_4^+$) or also tetralkylammonium ($N(C_1$-$C_8$-alkyl)$_4^+$, preferably $N(C_1$-$C_4$-alkyl)$_4^+$). Particularly preferred in the process according to the invention are those compounds Kat-X wherein Kat denotes cations which are formed by lithium, sodium, potassium, magnesium, calcium, ammonium or $N(C_1$-$C_4$-alkyl)$_4^+$. In the case of polyvalent cations, the salts formed by them ((such as e.g. $MgI_2$) are covered according to the invention by the designation "Kat-X", which should not therefore be regarded as being restricted to salts of a stoichiometric composition.

Of outstanding importance according to the invention are salts which are formed by sodium, potassium or ammonium, preferably sodium, tetrabutylammonium or ammonium, preferably sodium or ammonium.

The process according to the invention is preferably carried out in a polar solvent. It is particularly preferable to use solvents in which both the reagent Kat-X used and the resulting by-product Kat-Y are soluble.

Suitable solvents are easily recognised by the skilled man by certain routine experiments. Solvents in which the products of formula 1 are less soluble for example at ambient temperature (about 20-25° C.) than the components Kat-X and Kat-Y are particularly preferred according to the invention, as they assist particularly in the working up of the reaction. Preferred solvents are protic solvents such as alcohols (for example methanol, ethanol, isopropanol) and water, preferably water of pH 2-6 as well as polar organic solvents selected from the group consisting of alcohols such as for example ethyleneglycol and diethyleneglycol, amides such as for example dimethylformamide and N-methyl-pyrrolidinone, ethers such as for example tetrahydrofuran, dioxane, dimethylether and nitrites such as for example acetonitrile. It is particularly preferable to use water, methanol, ethanol, isopropanol, ethyleneglycol, diethyleneglycol, dimethylformamide, N-methyl-pyrrolidinone, tetrahydrofuran, dioxane, dimethylether or acetonitrile as solvent, while water, particularly aqueous solutions with a pH of about 2-6 are particularly preferred according to the invention.

In order to carry out the process according to the invention, at least stoichiometric amounts of the reagent Kat-X are required, based on the starting compound 2 used. However, it is preferable according to the invention to use the reagent Kat-X in excess. Preferably at least 2 equivalents, preferably at least 5 equivalents, particularly preferably at least 10 equivalents, more preferably at least 50 equivalents of Kat-X are used based on the compound 2 used. Basically, reactions wherein the excess of Kat-X is as great as possible are preferred according to the invention. The solubility of the reagent Kat-X must be taken into consideration, depending on the choice of solvent to be used. It is particularly preferable according to the invention to use saturated solutions of the reagent Kat-X.

The reaction according to the invention is preferably carried out by taking up the compound of formula 2 in solutions saturated with Kat-X and reacting at a temperature from at least 0° C. to at most the boiling temperature of the solvent used. Preferably, however, the reaction is carried out at less than 100° C., particularly preferably at less than 80° C., more preferably at less than 60° C. Particularly preferably, the reaction takes place according to the invention at a temperature in the range from 10-40° C., preferably at about 20-30° C. By comparison with reaction at higher temperatures, temperatures in the range from about 10-40° C. may lead to longer reaction times. However, reaction temperatures in the range from about 10-40° C. are preferred because of the non-aggressive reaction conditions according to the invention. In order to work up the reaction the compounds of formula 1 are filtered off and recrystallised if necessary.

The reactions according to the invention may also be carried out using ion exchangers known in the art. These ion exchangers are materials known in the art. For example materials selected from the group consisting of styrene, styrene-divinylbenzene (styrene-DVB) or polyacrylic may be used for this. Particularly preferably, resins are used which have cationic functional groups and may therefore be charged with the above-mentioned anions $X^-$. Examples include styrene-DVB with functional groups selected from $-NMe_3^+$, $-NMe_2(CH_2CH_2OH)^+$ or $-NH_3^+$. These resins are known in the art and commercially obtainable. By the action of solutions containing Kat-X, these ion exchange resins may be charged with the corresponding ions $X^-$. Solutions of the starting compounds of formula 2 in one of the above-mentioned solvents may be brought into contact according to the invention with the ion exchange resins charged with $X^-$. The solutions obtained after removal of the ion exchanger or after passing through correspondingly charged ion exchange columns contain the compounds of formula 1. These may be obtained from them in highly pure form.

In a preferred process according to the invention, the starting products used are compounds of formula 2 wherein
$Y^-$ denotes an anion other than $X^-$ selected from the group consisting of fluoride, chloride, bromide, iodide, $C_1$-$C_4$-alkylsulphate, or
$C_1$-$C_4$-alkylsulphonate, which may optionally be mono- or polysubstituted by fluorine at the alkyl group, or
phenylsulphonate, while the phenylsulphonate may optionally be mono- or polysubstituted at the phenyl ring by $C_1$-$C_4$-alkyl, preferably methyl.

Also preferred according to the invention is the preceding process wherein the starting products used are compounds of formula 2 wherein
$Y^-$ denotes an anion other than $X^-$ selected from the group consisting of fluoride, chloride, bromide, iodide, methylsulphate, ethylsulphate, methanesulphonate, ethanesulphonate, fluoromethanesulphonate, difluoromethanesulphonate, trifluoromethanesulphonate, phenylsulphonate and toluenesulphonate.

Preferred is the preceding process wherein the starting products used are compounds of formula 2 wherein
$Y^-$ denotes an anion other than $X^-$ selected from the group consisting of chloride, bromide, iodide, methylsulphate, ethylsulphate, methanesulphonate, trifluoromethanesulphonate and toluenesulphonate.

Particularly preferred is the preceding process wherein the starting products used are compounds of formula 2 wherein
$Y^-$ denotes an anion other than $X^-$ selected from the group consisting of bromide, methylsulphate, methanesulphonate, trifluoromethanesulphonate and toluenesulphonate, preferably bromide, methylsulphate or methanesulphonate.

Particularly preferably, using the process described above, salts 1 are obtained, wherein
$X^-$ denotes an anion selected from the group consisting of fluoride, chloride, bromide, iodide, $C_1$-$C_4$-alkylsulphate, sulphate, hydrogen sulphate, phosphate, hydrogen phosphate, dihydrogen phosphate, nitrate, maleate, acetate, trifluoroacetate, citrate, fumarate, tartrate, oxalate, succinate and benzoate, or
$C_1$-$C_4$-alkylsulphonate, which may optionally be mono-, di- or trisubstituted by fluorine at the alkyl group, or
phenylsulphonate, while the phenylsulphonate may optionally be mono- or polysubstituted by $C_1$-$C_4$-alkyl at the phenyl ring.

Particularly preferably, using the above-mentioned process, salts 1 are also obtained wherein
$X^-$ denotes an anion selected from the group consisting of fluoride, chloride, iodide, methylsulphate, ethylsulphate, sulphate, hydrogen sulphate, phosphate, hydrogen phosphate, dihydrogen phosphate, nitrate, maleate, acetate, trifluoroacetate, citrate, fumarate, tartrate, oxalate, succinate, benzoate, methanesulphonate, ethanesulphonate, fluoromethanesulphonate, difluoromethanesulphonate, trifluoromethanesulphonate, phenylsulphonate and toluenesulphonate.

Preferably, according to the invention, using the above-mentioned process, salts 1 are also obtained wherein
$X^-$ is selected from fluoride, chloride, iodide, nitrate, maleate, acetate, trifluoroacetate, benzoate, methanesulphonate, trifluoromethanesulphonate and toluenesulphonate, while preferably salts 1 wherein $X^-$ is selected from chloride, iodide, acetate, trifluoroacetate and benzoate, preferably chloride and iodide are obtained by the process according to the invention.

The present invention also relates to the use of the compounds of formula 2 wherein Y⁻ may have the meanings given above, as a starting compound for preparing the compounds of formula 1.

$C_1$-$C_{10}$ alkyl, unless otherwise stated, refers to branched and unbranched alkyl groups with 1 to 10 carbon atoms, preferably 1 to 4 carbon atoms. The following are mentioned by way of example: methyl, ethyl, propyl or butyl. In some cases the abbreviations Me, Et, Prop or Bu are used to denote the groups methyl, ethyl, propyl or butyl. Unless otherwise stated, the definitions propyl and butyl include all the possible isomeric forms of the groups in question. Thus, for example, propyl includes n-propyl and iso-propyl, butyl includes iso-butyl, sec.butyl and tert.-butyl, etc.

Unless otherwise stated alkyl groups may also optionally substituted if they are part of other groups (e.g. alkylsulphonate), for example by one or more groups selected from the group consisting of fluorine, chlorine, bromine, $CF_3$, hydroxy or methoxy.

Halogen within the scope of the present invention represents fluorine, chlorine, bromine or iodine.

The term $C_6$-$C_{10}$-aryl denotes an aromatic ring system with 6 to 10 carbon atoms. Preferred aryl groups are phenyl or naphthyl. These may optionally be substituted, for example by one or more groups selected from the group comprising methyl, fluorine, chlorine, bromine, hydroxy, $CF_3$ or methoxy.

The starting compounds of formula 2 are prepared for example analogously to the method disclosed in EP-A-418716. This is outlined in the following Diagram 1.

Diagram 1:

Starting from scopinedithienylglycolic acid esters 3 the starting compounds 2 may be obtained by reaction with the reagent Me-Y.

The prior art has hitherto only described the synthesis of tiotropium bromide (according to Diagram 1). Inasmuch as the compounds of formula 2 wherein Y⁻ has a meaning other than bromide are novel and may be used like tiotropium bromide as starting compounds in the synthesis according to the invention for preparing the compounds of formula 1, the present invention also relates to the starting compounds of formula 2 as such, wherein Y⁻ may have all the meanings given above, with the exception of bromide, optionally in the form of the solvates or hydrates thereof.

For example using this method the following starting compounds of formula 2 which have not yet been described in the art and which are also preferred according to the invention are obtained:

scopine di-(2-thienyl)glycolate-methomethanesulphonate (tiotropium methanesulphonate);
scopine di-(2-thienyl)glycolate-methomethylsulphate (tiotropium methylsulphate).

Where these new compounds may be used as starting compounds in the process according to the invention, the present invention relates particularly preferably to the two above-mentioned compounds as such, optionally in the form of the solvates or hydrates thereof.

The following Examples serve to illustrate the present invention more fully, without restricting the scope of the invention to the embodiments described by way of example.

A.I. Starting Materials

A.I.1. Tiotropium bromide:

Tiotropium bromide may be obtained for example using the procedure described in European Patent Application EP 418 716.

A.I.2. Tiotropium Methanesulphonate:

75.5 g scopine di-(2-thienyl)glycolate are dissolved in 750 ml acetonitrile while heating gently. After the addition of 22 ml of methyl methanesulphonate the mixture is stirred at 55° C. After the reaction has ended about 350 ml solvent distilled off under reduced pressure. The product crystallises out and is filtered off. It is purified by recrystallisation from methanol/acetone.

Yield: 83.35 g white crystals (74.3%); melting point: 229-231° C. (with decomposition).

A.I.3. Tiotropium Methylsulphate:

Analogously to the method described in para. 1.2, 75.5 g scopine di-(2-thienyl)glycolate are reacted with 20.9 ml dimethylsulphate in 750 ml acetonitrile.

The crude product which crystallises out is separated off and recrystallised from methanol for purification.

Yield: 83.89 g white crystals (77.5%); melting point: 183-184° C. (with decomposition).

A.II. Examples of Synthesis According to the Invention

Example 1

Tiotropium Chloride 1.00 g tiotropium bromide is suspended in 100 ml saturated NaCl solution (35.8 g NaCl/100 g E-water) and stirred for 14 h at ambient temperature. It is then filtered and the product thus obtained is suspended again for 4 h in 100 ml saturated NaCl— solution (35.8 g/100 g). The product is isolated by filtration, dried and then taken up in 15 ml of methanol at boiling temperature. It is filtered hot to remove insoluble matter and the filtrate is cooled to ambient temperature, whereupon the product crystallises out.

Yield: 486.2 mg (53.7%); colourless crystal powder; melting point: 234° C. (decomposition);

Anions detected by HPLC: chloride 7.99% (calc: 8.28%); the bromide can no longer be detected.

Example 2

Tiotropium Iodide 5.00 g of tiotropium bromide are suspended in 50 ml saturated. ammonium iodide solution (85 g $NH_4I$/50 g water) and stirred for 2 days at ambient temperature. It is then filtered, the product thus obtained is dried and then taken up in 85 ml of methanol at boiling temperature. It is filtered hot to remove insoluble matter and the filtrate is cooled to ambient temperature, whereupon the product crystallises out.

Yield: 4.41 g (80%); colourless crystal powder; melting point 205° C.;

Anions detected by HPLC: iodide 24.28% (calc: 24.43%); the bromide can no longer be detected.

The products 1 obtained are obtained analogously starting from tiotropium methylsulphate or tiotropium methanesulphonate.

A.III. Characterisation of the Examples of Synthesis According to the Invention

The compounds obtained by the above process were characterised in more detail using X-ray powder diffraction. The following procedure was used to record the X-ray powder diagrams listed below.

The X-ray powder diagrams were recorded within the scope of the present invention using a Bruker D8 Advanced with an OED (=location-sensitive detector) (CuK$_\alpha$-radiation, $\lambda$=1.5418 Å, 30 kV, 40 mA).

Example 1

Tiotropium Chloride

The tiotropium chloride obtained by the above method is highly crystalline and is obtained in anhydrous form. It was subjected to further examination by X-ray powder diffraction.

The X-ray powder diagram obtained for the anhydrous tiotropium chloride is shown in FIG. 1.

Table 1 below lists the characteristic peaks and standardised intensities.

TABLE 1

| 2 Θ [°] | d$_{hkl}$ [Å] | intensity [%] |
|---|---|---|
| 8.83 | 10.01 | 6 |
| 11.87 | 7.45 | 31 |
| 13.2 | 6.7 | 8 |
| 13.82 | 6.4 | 8 |
| 14.39 | 6.15 | 83 |
| 15.29 | 5.79 | 9 |
| 15.87 | 5.58 | 100 |
| 16.72 | 5.3 | 12 |
| 17.24 | 5.14 | 44 |
| 17.68 | 5.01 | 45 |
| 18.22 | 4.86 | 4 |
| 19.38 | 4.58 | 4 |
| 19.95 | 4.45 | 86 |
| 20.85 | 4.26 | 20 |
| 21.45 | 4.14 | 4 |
| 22.59 | 3.93 | 53 |
| 23.47 | 3.79 | 16 |
| 24.09 | 3.69 | 18 |
| 24.48 | 3.63 | 5 |
| 24.84 | 3.58 | 10 |
| 25.56 | 3.48 | 9 |
| 26.12 | 3.41 | 25 |
| 26.53 | 3.36 | 4 |
| 27.41 | 3.25 | 44 |
| 27.83 | 3.2 | 4 |
| 28.76 | 3.1 | 7 |
| 29.59 | 3.02 | 7 |
| 29.86 | 2.99 | 10 |
| 30.49 | 2.93 | 4 |

In the above Table the value "2 Θ [°]" represents the diffraction angle in degrees and the value "d$_{hkl}$ [Å]" represents the specified lattice plane intervals in A.

The tiotropium chloride obtained by the method of synthesis according to the invention is highly crystalline and is therefore particularly well suited to the preparation of, for example, pharmaceutical formulations for administration by inhalation such as inhalable powders or for example propellant-containing aerosol formulations.

Accordingly, the present invention also relates to tiotropium chloride as such, particularly crystalline tiotropium chloride, optionally in the form of the hydrates or solvates thereof. Particularly preferred is a crystalline tiotropium chloride which is characterised in that in the X-ray powder diagram it has, inter alia, the characteristic values d=6.15 Å; 5.58 Å; 4.45 Å and 3.93 Å.

The tiotropium chloride which may be obtained by the above method can be converted directly into the corresponding hydrate by the controlled action of moisture (i.e. water vapour or the like). Accordingly, the present invention also relates to the above-mentioned tiotropium chloride in the form of its hydrate.

Example 2

Tiotropium Iodide

The tiotropium iodide obtained by the above method is highly crystalline and is obtained in anhydrous form. It was further investigated by X-ray powder diffraction.

The X-ray powder diagram obtained for the anhydrous tiotropium iodide is shown in FIG. 2.

Table 2 below lists the characteristic peaks and standardised intensities.

TABLE 2

| 2 Θ [°] | d$_{hkl}$ [Å] | intensity [%] |
|---|---|---|
| 11.00 | 8.04 | 5 |
| 12.32 | 7.18 | 23 |
| 13.15 | 6.73 | 15 |
| 14.04 | 6.30 | 31 |
| 15.03 | 5.89 | 13 |
| 15.68 | 5.65 | 13 |
| 16.36 | 5.41 | 11 |
| 17.07 | 5.19 | 30 |
| 17.29 | 5.12 | 15 |
| 17.88 | 4.96 | 26 |
| 18.18 | 4.88 | 8 |
| 18.44 | 4.81 | 25 |
| 19.84 | 4.47 | 100 |
| 20.09 | 4.42 | 26 |
| 21.61 | 4.11 | 44 |
| 22.42 | 3.96 | 11 |
| 22.69 | 3.92 | 11 |
| 22.82 | 3.89 | 7 |
| 23.38 | 3.8 | 28 |
| 25.04 | 3.55 | 38 |
| 25.36 | 3.51 | 9 |
| 26.35 | 3.38 | 11 |
| 26.50 | 3.36 | 13 |
| 26.69 | 3.34 | 27 |
| 26.99 | 3.30 | 8 |
| 27.31 | 3.26 | 4 |
| 27.78 | 3.21 | 15 |
| 28.13 | 3.17 | 19 |
| 28.33 | 3.15 | 14 |
| 28.68 | 3.11 | 7 |
| 28.98 | 3.08 | 6 |
| 29.20 | 3.06 | 7 |
| 29.47 | 3.03 | 16 |
| 29.97 | 2.98 | 5 |
| 30.31 | 2.95 | 6 |
| 31.54 | 2.83 | 18 |
| 32.11 | 2.78 | 20 |

In the above Table the value "2 Θ [°]" represents the diffraction angle in degrees and the value "$d_{hkl}$ [Å]" represents the specified lattice plane intervals in A.

The tiotropium iodide obtained by the method of synthesis according to the invention is highly crystalline and is therefore particularly well suited to the preparation of, for example, pharmaceutical formulations for administration by inhalation such as inhalable powders or for example propellant-containing aerosol formulations.

Accordingly, the present invention also relates to tiotropium iodide as such, particularly crystalline tiotropium iodide, optionally in the form of the hydrates or solvates thereof. Particularly preferred is the anhydrous crystalline tiotropium iodide according to the invention which is characterised in that in the X-ray powder diagram it has, inter alia, the characteristic values d=6.30 Å; 5.19 Å; 4.47 Å; 4.11 Å and 3.55 Å.

B. Pharmaceutical Formulations

The present invention also relates to new pharmaceutical formulations which contain the above-mentioned new tiotropium salts tiotropium chloride or tiotropium iodide. Tiotropium chloride and tiotropium iodide are preferably administered by inhalation. This may be done using inhalable powdered formulations, propellant-containing aerosol formulations or propellant-free inhalable solutions.

B.1. Inhalable Powder

The present invention also relates to inhalable powder containing 0.001 to 3% tiotropium in the form of the tiotropium chloride or tiotropium iodide according to the invention combined with a physiologically acceptable excipient. By tiotropium is meant the ammonium cation.

Inhalable powders which contain 0.01 to 2% tiotropium are preferred according to the invention. Particularly preferred inhalable powders contain tiotropium in an amount from about 0.03 to 1%, preferably 0.05 to 0.6%, particularly preferably 0.06 to 0.3%. Of particular importance according to the invention, finally, are inhalable powders which contain about 0.08 to 0.22% tiotropium.

The amounts of tiotropium specified above are based on the amount of tiotropium cation contained. The inhalable powders according to the invention contain tiotropium in the form of the tiotropium chloride or tiotropium iodide according to the invention.

The excipients that are used for the purposes of the present invention are prepared by suitable grinding and/or screening using current methods known in the art. The excipients used according to the invention may also be mixtures of excipients which are obtained by mixing excipient fractions of different mean particle sizes.

Examples of physiologically acceptable excipients which may be used to prepare the inhalable powders used to produce the inhalable powders for use in the inhalettes according to the invention include monosaccharides (e.g. glucose, fructose or arabinose), disaccharides (e.g. lactose, saccharose, maltose, trehalose), oligo- and polysaccharides (e.g. dextrans, dextrins, maltodextrin, starch, cellulose), polyalcohols (e.g. sorbitol, mannitol, xylitol), cyclodextrins (e.g. α-cyclodextrin, β-cyclodextrin, χ-cyclodextrin, methyl-β-cyclodextrin, hydroxypropyl-β-cyclodextrin), amino acids (e.g. arginine hydrochloride) or salts (e.g. sodium chloride, calcium carbonate), or mixtures thereof. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 μm, preferably between 10 and 150 μm, most preferably between 15 and 80 μm. It may sometimes seem appropriate to add finer excipient fractions with an average particle size of 1 to 9 μm to the excipients mentioned above. These finer excipients are also selected from the group of possible excipients listed hereinbefore. The average particle size may be determined using methods known in the art (cf. for example WO 02/30389, paragraphs A and C). Finally, in order to prepare the inhalable powder according to the invention, micronised tiotropium chloride or tiotropium iodide, which preferably characterised by an average particle size of 0.5 to 10 μm, particularly preferably from 1 to 5 μm, is added to the excipient mixture. The average particle size may be determined using methods known in the art (cf. for example WO 02/30389, paragraph B). Processes for grinding and micronising active substances are known from the prior art.

If no specifically prepared excipient mixture is used as the excipient, it is particularly preferable to use excipients which have a mean particle size of 10-50 μm and a 10% fine content.

By average particle size is meant here the 50% value of the volume distribution measured with a laser diffractometer using the dry dispersion method. The average particle size may be determined using methods known in the art (cf. for example WO 02/30389, paragraphs A and C). Analogously, the 10% fine content in this instance refers to the 10% value of the volume distribution measured using a laser diffractometer. In other words, for the purposes of the present invention, the 10% fine content denotes the particle size below which 10% of the quantity of particles is found (based on the volume distribution).

The percentages given within the scope of the present invention are always percent by weight, unless specifically stated to the contrary.

In particularly preferred inhalable powders the excipient is characterised by a mean particle size of 12 to 35 μm, particularly preferably from 13 to 30 μm.

Also particularly preferred are those inhalable powders wherein the 10% fine content is about 1 to 4 μm, preferably about 1.5 to 3 μm.

The inhalable powders according to the invention are characterised, in accordance with the problem on which the invention is based, by a high degree of homogeneity in the sense of the accuracy of single doses. This is in the region of <8%, preferably <6%, most preferably <4%.

After the starting materials have been weighed out the inhalable powders are prepared from the excipient and the active substance using methods known in the art. Reference may be made to the disclosure of WO 02/30390, for example. The inhalable powders according to the invention may accordingly be obtained by the method described below, for example. In the preparation methods described hereinafter the components are used in the proportions by weight described in the above-mentioned compositions of the inhalable powders.

First, the excipient and the active substance are placed in a suitable mixing container. The active substance used has an average particle size of 0.5 to 10 μm, preferably 1 to 6 μm, most preferably 2 to 5 μm. The excipient and the active substance are preferably added using a sieve or a granulating sieve with a mesh size of 0.1 to 2 mm, preferably 0.3 to 1 mm, most preferably 0.3 to 0.6 mm. Preferably, the excipient is put in first and then the active substance is added to the mixing container. During this mixing process the two components are preferably added in batches. It is particularly preferred to sieve in the two components in alternate layers. The mixing of the excipient with the active substance may take place while the two components are still being added. Preferably, however, mixing is only done once the two components have been sieved in layer by layer.

The present invention also relates to the use of the inhalable powders according to the invention for preparing a pharmaceutical composition for the treatment of respiratory complaints, particularly for the treatment of COPD and/or asthma.

The inhalable powders according to the invention may for example be administered using inhalers which meter a single dose from a reservoir by means of a measuring chamber (e.g. according to U.S. Pat. No. 4,570,630A) or by other means (e.g. according to DE 36 25 685 A). Preferably, however, the inhalable powders according to the invention are packed into capsules (to make so-called inhalettes), which are used in inhalers such as those described in WO 94/28958, for example.

Figure 3:
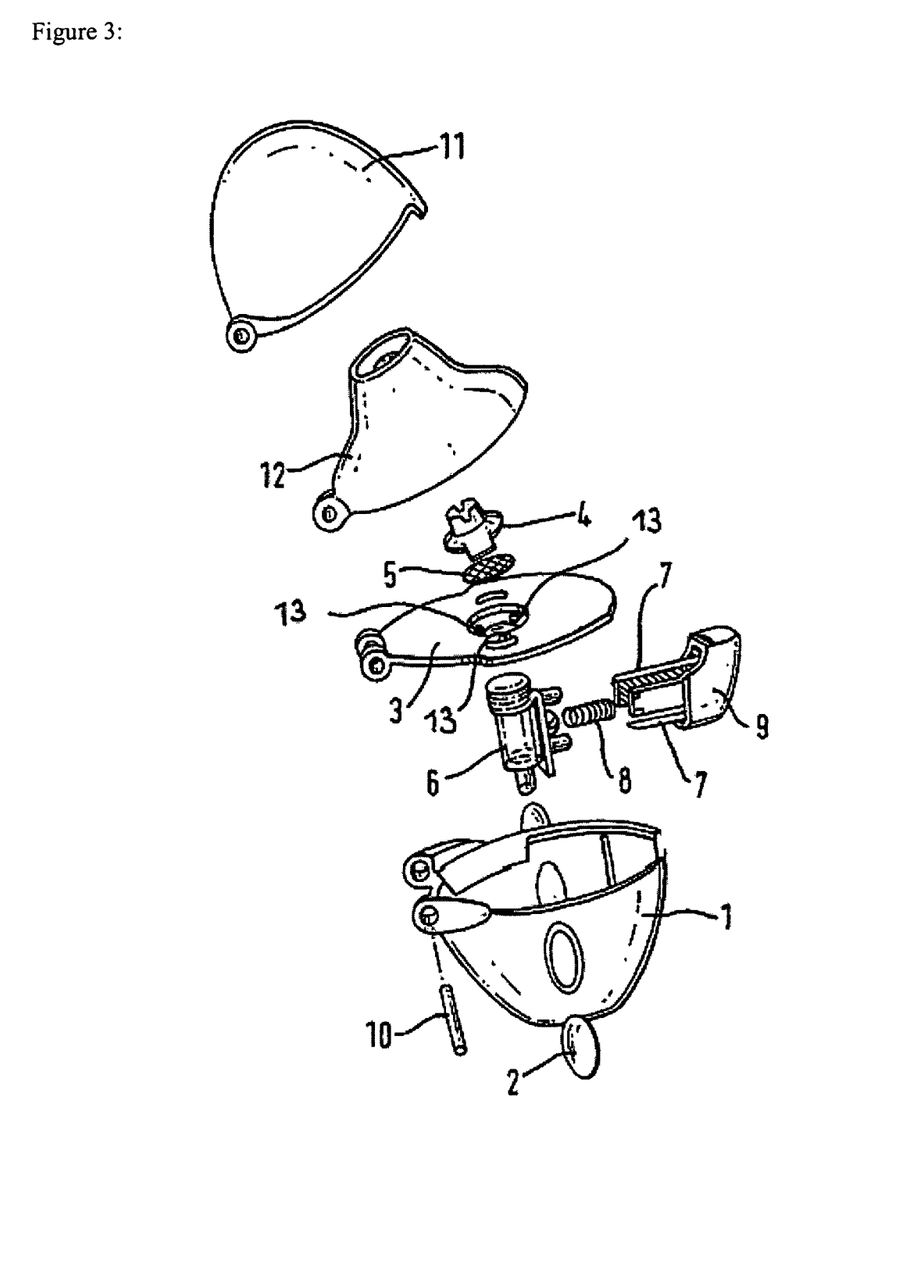

Most preferably, the capsules containing the inhalable powder according to the invention are administered using an inhaler as shown in FIG. 3. This inhaler is characterised by a housing 1 containing two windows 2, a deck 3 in which there are air inlet ports and which is provided with a screen 5 secured via a screen housing 4, an inhalation chamber 6 connected to the deck 3 on which there is a push button 9 provided with two sharpened pins 7 and movable counter to a spring 8, and a mouthpiece 12 which is connected to the housing 1, the deck 3 and a cover 11 via a spindle 10 to enable it to be flipped open or shut and airholes 13 for adjusting the flow resistance.

The present invention further relates to the use of the inhalable powders according to the invention for preparing a pharmaceutical composition for treating respiratory complaints, particularly for the treatment of COPD and/or asthma, characterised in that the inhaler described above and shown in FIG. 3 is used.

For administering the inhalable powders according to the invention using powder-filled capsules it is particularly preferred to use capsules the material of which is selected from among the synthetic plastics, most preferably selected from among polyethylene, polycarbonate, polyester, polypropylene and polyethylene terephthalate. Particularly preferred synthetic plastic materials are polyethylene, polycarbonate or polyethylene terephthalate. If polyethylene is used as one of the capsule materials which is particularly preferred according to the invention, it is preferable to use polyethylene with a density of between 900 and 1000 kg/m$^3$, preferably 940-980 kg/m$^3$, more preferably about 960-970 kg/m$^3$ (high density polyethylene).

The synthetic plastics according to the invention may be processed in various ways using manufacturing methods known in the art. Injection moulding of the plastics is preferred according to the invention. Injection moulding without the use of mould release agents is particularly preferred. This method of production is well defined and is characterised by being particularly reproducible.

In another aspect the present invention relates to the abovementioned capsules which contain the abovementioned inhalable powders according to the invention. These capsules may contain about 1 to 20 mg, preferably about 3 to 15 mg, most preferably about 4 to 12 mg of inhalable powder. Preferred formulations according to the invention contain 4 to 6 mg of inhalable powder. Of equivalent importance according to the invention are capsules for inhalation which contain the formulations according to the invention in an amount of from 8 to 12 mg.

The present invention also relates to an inhalation kit consisting of one or more of the above capsules characterised by a content of inhalable powder according to the invention in conjunction with the inhaler according to FIG. 3.

The present invention also relates to the use of the abovementioned capsules characterised by a content of inhalable powder according to the invention, for preparing a pharmaceutical composition for treating respiratory complaints, especially for treating COPD and/or asthma.

Filled capsules which contain the inhalable powders according to the invention are produced by methods known in the art, by filling the empty capsules with the inhalable powders according to the invention.

B.1.1. Examples of Inhalable Powders According to the Invention

The following Examples serve to illustrate the present invention in more detail without restricting the scope of the invention to the exemplifying embodiments that follow.

B.1.1.1. Starting Materials

Active Substance

The tiotropium chloride or tiotropium iodide according to the invention are used to prepare the inhalable powders according to the invention. These active substances are micronised analogously to methods known in the art (cf. for example WO 03/078429 A1).

Excipient:

In the Examples that follow lactose-monohydrate is used as excipient. It may be obtained for example from Borculo Domo Ingredients, Borculo/NL under the product name Lactochem Extra Fine Powder. The specifications according to the invention for the particle size and specific surface area are met by this grade of lactose.

B.1.1.2. Preparation of the Powder Formulations According to the Invention:

I) Apparatus

The following machines and equipment, for example, may be used to prepare the inhalable powders:

Mixing container or powder mixer: Turbulamischer 2 L, Type 2C; made by Willy A. Bachofen AG, CH-4500 Basel Hand-held screen: 0.135 mm mesh size The empty inhalation capsules may be filled with inhalable powders containing tiotropium by hand or mechanically. The following equipment may be used.

Capsule Filling Machine:

MG2, Type G100, manufacturer: MG2 S.r.l, 1-40065 Pian di Macina di Pianoro (BO), Italy Formulation Example 1

Powder Mixture:

To prepare the powder mixture, 299.39 g of excipient and 0.61 g of micronised tiotropium chloride (or tiotropium iodide) are used. In the resulting 300 g of inhalable powder the content of active substance, based on tiotropium, is 0.19% in the case of tiotropium chloride and 0.15% in the case of tiotropium iodide.

About 40-45 g of excipient are placed in a suitable mixing container through a hand-held screen with a mesh size of 0.315 mm. Then tiotropium chloride (or tiotropium iodide) in batches of about 90-110 mg and excipient in batches of about 40-45 g are screened in in alternate layers. The excipient and active substance are added in 7 and 6 layers, respectively.

Having been screened in, the ingredients are then mixed (mixing speed 900 rpm). The final mixture is passed twice more through a hand-held screen and then mixed again at 900 rpm.

Using the method described in Example 1 it is possible to obtain inhalable powders which when packed into suitable plastic capsules may be used to produce the following capsules for inhalation, for example:

Formulation Example 2

| | |
|---|---|
| tiotropium chloride: | 0.0113 mg |
| lactose monohydrate: | 5.4887 mg |
| polyethylene capsules: | 100.0 mg |
| Total: | 105.5 mg |

Formulation Example 3

| | |
|---|---|
| tiotropium chloride: | 0.0113 mg |
| lactose monohydrate*): | 5.4887 mg |
| polyethylene capsules: | 100.0 mg |
| Total: | 105.5 mg |

*)the lactose contains 5% specifically added fine content of micronised lactose monohydrate with an average particle size of about 4 μm.

Formulation Example 4

| | |
|---|---|
| tiotropium iodide: | 0.0113 mg |
| lactose monohydrate: | 5.4887 mg |
| polyethylene capsules: | 100.0 mg |
| Total: | 105.5 mg |

Formulation Example 5

| | |
|---|---|
| tiotropium iodide: | 0.0225 mg |
| lactose monohydrate: | 5.4775 mg |
| polyethylene capsules: | 100.0 mg |
| Total: | 105.5 mg |

Formulation Example 6

| | |
|---|---|
| tiotropium chloride: | 0.0056 mg |
| lactose monohydrate: | 5.4944 mg |
| polyethylene capsules: | 100.0 mg |
| Total: | 105.5 mg |

Formulation Example 7

| | |
|---|---|
| tiotropium chloride: | 0.0056 mg |
| lactose monohydrate*): | 5.4944 mg |
| polyethylene capsules: | 100.0 mg |
| Total: | 105.5 mg |

*)the lactose contains 5% specifically added fine content of micronised lactose monohydrate with an average particle size of about 4 μm.

Formulation Example 8

| | |
|---|---|
| tiotropium iodide: | 0.0113 mg |
| lactose monohydrate*): | 9.9887 mg |
| polyethylene capsules: | 100.0 mg |
| Total: | 110.0 mg |

*)the lactose contains 5% specifically added fine content of micronised lactose monohydrate with an average particle size of about 4 μm.

Formulation Example 9

| | |
|---|---|
| tiotropium iodide: | 0.0225 mg |
| lactose monohydrate*): | 9.9775 mg |
| polyethylene capsules: | 100.0 mg |
| Total: | 110.0 mg |

*)the lactose contains 5% specifically added fine content of micronised lactose monohydrate with an average particle size of about 4 μm.

B.2. Propellant-Containing Inhalable Aerosols

The new tiotropium salts tiotropium chloride or tiotropium iodide may optionally also be administered in the form of propellant-containing inhalable aerosols. Aerosol formulations in the form of solutions or suspensions may be used for this.

B.2.1. Aerosol Formulations in the Form of Solutions

The term aerosol solution denotes pharmaceutical formulations in which the tiotropium chloride or iodide and any excipients used are completely dissolved.

The present invention provides aerosol formulations containing tiotropium chloride and iodide, which contain in addition to one of the above-mentioned tiotropium salts an HFA propellant, a co-solvent and an inorganic or organic acid and which are further characterised in that the concentration of the acid is such that in aqueous solution it corresponds to a pH in the range from 2.5-4.5.

The above-mentioned aerosol solutions are characterised by a particularly high stability.

Preferred aerosol solutions are characterised in that the concentration of the acid is such that in aqueous solution it corresponds to a pH in the range from 3.0-4.3, particularly preferably from 3.5-4.0.

The aerosol solutions according to the invention may also contain a small amount of water (preferably up to 5%, particularly preferably up to 3%, more preferably up to 2%).

The aerosol solutions according to the invention preferably contain an amount of tiotropium chloride or tiotropium iodide such that the proportion of tiotropium cation they contain is between 0.00008 and 0.4%, preferably between 0.0004 and 0.16%, particularly preferably between 0.0008 and 0.08%.

Suitable HFA propellants within the scope of the aerosol solutions are those which form a homogeneous propellant formulation with the co-solvents used, in which a therapeutically effective amount of the tiotropium chloride or iodide may be dissolved.

Preferred HFA propellants according to the invention are propellants selected from the group consisting of 1,1,1,2-tetrafluoroethane (HFA-134(a)), 1,1,1,2,3,3,3,-heptafluoropropane (HFA-227), HFA-32 (difluoromethane), HFA-143 (a) (1.1.1-trifluoroethane), HFA-134 (1,1,2,2-tetrafluoroethane) and HFA-152a (1,1-difluoroethane. HFA-134(a) and HFA-227 are particularly preferred according to the invention, while HFA-134(a) is particularly important according to the invention. In addition to the HFA propellants mentioned above, non-halogenated propellants may also be used on their own or mixed with one or more of the abovementioned HFA propellants. Examples of such non-halogenated propellants are saturated hydrocarbons such as for example n-propane, n-butane or isobutane, or also ethers such as diethyl ether, for example.

Organic or inorganic acids may be used as acids according to the invention. Inorganic acids within the scope of the present invention are selected for example from the group consisting of hydrochloric acid, sulphuric acid, nitric acid or phosphoric acid, while according to the invention it is preferable to use hydrochloric or sulphuric acid, particularly hydrochloric acid. Organic acids within the scope of the present invention are selected for example from the group consisting of ascorbic acid, citric acid, lactic acid, maleic acid, benzoic acid or tartaric acid, while ascorbic acid and citric acid are preferred according to the invention.

The aerosol solutions according to the invention may be obtained analogously to methods known in the art.

Pharmaceutically acceptable excipients may optionally be contained in the aerosol solutions according to the invention. For example, soluble surfactants and lubricants may be used. Examples of such soluble surfactants and lubricants include sorbitan trioleate, lecithin or isopropyl myristate. Other excipients which may be present may be antioxidants (for example ascorbic acid or tocopherol), flavour masking agents (for example menthol, sweeteners and synthetic or natural flavourings).

Examples of co-solvents which may be used according to the invention are alcohols (for example ethanol, isopropanol and benzylalcohol), glycols (for example propyleneglycol, polyethyleneglycols, polypropyleneglycol, glycolether, block copolymers of oxyethylene and oxypropylene) or other substances such as for example glycerol, polyoxyethylene alcohols, polyoxyethylene fatty acid esters and glycofurols (such as for example glycofurol 75). A preferred co-solvent according to the invention is ethanol.

The amount of co-solvents which may be used in the formulations according to the invention is preferably in the range from 5-50%, preferably 10-40%, particularly preferably 15-30% based on the total formulation.

Unless stated to the contrary, the percentages specified within the scope of the present invention are to be read as percent by weight.

The formulations according to the invention may contain small amounts of water, as already mentioned previously. In a preferred aspect, the present invention relates to formulations in which the content of water is up to 5%, particularly preferably up to 3%, more preferably up to 2%.

In another aspect the present invention relates to aerosol solutions which contain no water. In these formulations the amount of cosolvent is preferably in the range from 20-50%, preferably in the range from 30-40%.

The formulations according to the invention may be administered using inhalers known in the art (pMDIs=pressurized metered dose inhalers).

The present invention also relates to the use of the abovementioned aerosol solutions characterised by a content of tiotropium chloride or iodide according to the invention for preparing a pharmaceutical composition for the treatment of respiratory complaints, particularly for the treatment of COPD and/or asthma.

The following Examples serve to illustrate the present invention in more detail without restricting the scope of the invention to the exemplifying embodiments that follow.

B.2.1.1 Examples of Aerosol Solutions

Formulation Example 10

| constituents | concentration [% w/w] |
|---|---|
| tiotropium iodide | 0.01 |
| ethanol (absolute) | 30.0 |
| water | 1.0 |
| ascorbic acid | 0.005 |
| HFA-134a | 68.985 |

Formulation Example 11

| constituents | concentration [% w/w] |
|---|---|
| tiotropium iodide | 0.01 |
| ethanol (absolute) | 40.0 |
| citric acid | 0.004 |
| HFA-227 | 59.986 |

Formulation Example 12

| constituents | concentration [% w/w] |
|---|---|
| tiotropium chloride | 0.02 |
| ethanol (absolute) | 25.0 |
| water | 1.0 |
| citric acid | 0.003 |
| HFA-134a | 73.977 |

Formulation Example 13

| constituents | concentration [% w/w] |
|---|---|
| tiotropium chloride | 0.02 |
| ethanol (absolute) | 20.0 |
| HCl (aq) 0.01 mol/l | 2.0 |
| HFA-134a | 77.98 |

Formulation Example 14

| constituents | concentration [% w/w] |
| --- | --- |
| tiotropium chloride | 0.01 |
| ethanol (absolute) | 15.0 |
| water | 2.0 |
| citric acid | 0.004 |
| HFA-227 | 82.986 |

Formulation Example 15

| constituents | concentration [% w/w] |
| --- | --- |
| tiotropium chloride | 0.01 |
| ethanol (absolute) | 30.0 |
| water | 1.0 |
| ascorbic acid | 0.005 |
| HFA-134a | 68.985 |

Formulation Example 16

| constituents | concentration [% w/w] |
| --- | --- |
| tiotropium chloride | 0.01 |
| ethanol (absolute) | 40.0 |
| citric acid | 0.004 |
| HFA-227 | 59.986 |

Formulation Example 17

| constituents | concentration [% w/w] |
| --- | --- |
| tiotropium iodide | 0.02 |
| ethanol (absolute) | 25.0 |
| water | 1.0 |
| citric acid | 0.003 |
| HFA-134a | 73.977 |

Formulation Example 18

| constituents | concentration [% w/w] |
| --- | --- |
| tiotropium iodide | 0.02 |
| ethanol (absolute) | 20.0 |
| HCl (aq) 0.01 mol/l | 2.0 |
| HFA-134a | 77.98 |

Formulation Example 19

| constituents | concentration [% w/w] |
| --- | --- |
| tiotropium iodide | 0.01 |
| ethanol (absolute) | 15.0 |
| water | 2.0 |
| citric acid | 0.004 |
| HFA-227 | 82.986 |

B.2.2. Aerosol Suspensions

The present invention also relates to suspensions of the tiotropium salts tiotropium chloride and tiotropium iodide according to the invention in the propellant gases HFA 227 and/or HFA 134a, optionally combined with one or more other propellant gases, preferably selected from the group consisting of propane, butane, pentane, dimethylether, $CHClF_2$, $CH_2F_2$, $CF_3CH_3$, isobutane, isopentane and neopentane.

According to the invention those suspensions which contain as propellant gas only HFA 227, a mixture of HFA 227 and HFA 134a or only HFA 134a are preferred.

If a mixture of the propellent gases HFA 227 and HFA 134a is used in the suspension formulations according to the invention, the weight ratios in which these two propellent gas components are used are freely variable.

If one or more other propellent gases, selected from the group consisting of propane, butane, pentane, dimethylether, $CHClF_2$, $CH_2F_2$, $CF_3CH_3$, isobutane, isopentane and neopentane are used in addition to the propellent gases HFA 227 and/or HFA 134a in the suspension formulations according to the invention, the amount of this additional propellent gas component is preferably less than 50%, preferably less than 40%, particularly preferably less than 30%.

The suspensions according to the invention preferably contain an amount of tiotropium chloride or iodide such that the amount of tiotropium cation is between 0.001 and 0.8%, preferably between 0.08 and 0.5%, and particularly preferably between 0.2 and 0.4% according to the invention.

Unless stated to the contrary, the percentages given within the scope of the present invention are always percent by weight.

In some cases, the term suspension formulation is used within the scope of the present invention instead of the term suspension. The two terms are to be regarded as equivalent within the scope of the present invention.

The propellant-containing inhalable aerosols or suspension formulations according to the invention may also contain other constituents such as surface-active agents (surfactants), adjuvants, antioxidants or flavourings.

The surface-active agents (surfactants) optionally present in the suspensions according to the invention are preferably selected from the group consisting of Polysorbate 20, Polysorbate 80, Myvacet 9-45, Myvacet 9-08, isopropyl myristate, oleic acid, propyleneglycol, polyethyleneglycol, Brij, ethyl oleate, glyceryl trioleate, glyceryl monolaurate, glyceryl monooleate, glyceryl monostearate, glyceryl monoricinoleate, cetylalcohol, sterylalcohol, cetylpyridinium chloride, block polymers, natural oil, ethanol and isopropanol. Of the above-mentioned suspension adjuvants Polysorbate 20, Polysorbate 80, Myvacet 9-45, Myvacet 9-08 or isopropyl myristate are preferably used. Myvacet 9-45 or isopropyl myristate are most preferably used.

If the suspensions according to the invention contain surfactants these are preferably used in an amount of 0.0005-1%, particularly preferably 0.005-0.5%.

The adjuvants optionally contained in the suspensions according to the invention are preferably selected from the group consisting of alanine, albumin, ascorbic acid, aspartame, betaine, cysteine, phosphoric acid, nitric acid, hydrochloric acid, sulphuric acid and citric acid. Ascorbic acid, phosphoric acid, hydrochloric acid or citric acid are preferably used, while hydrochloric acid or citric acid is most preferably used.

If adjuvants are present in the suspensions according to the invention, these are preferably used in an amount of 0.0001-1.0%, preferably 0.0005-0.1%, particularly preferably 0.001-0.01%, while an amount of 0.001-0.005% is particularly important according to the invention.

The antioxidants optionally contained in the suspensions according to the invention are preferably selected from the group consisting of ascorbic acid, citric acid, sodium edetate, editic acid, tocopherols, butylhydroxytoluene, butylhydroxyanisol and ascorbylpalmitate, while tocopherols, butylhydroxytoluene, butylhydroxyanisol or ascorbylpalmitate are preferably used.

The flavourings optionally contained in the suspensions according to the invention are preferably selected from the group consisting of peppermint, saccharine, Dentomint, aspartame and ethereal oils (for example cinnamon, aniseed, menthol, camphor), peppermint or Dentomint® being particularly preferred.

With a view to administration by inhalation it is essential to provide the active substances in finely divided form. For this purpose, the salts tiotropium chloride and iodide according to the invention are either ground (micronised) or obtained in finely divided form by other technical processes known in principle from the prior art (for example precipitation, spray drying). Methods of micronising active substances are known in the art. Preferably after micronising the active substance has a mean particle size of 0.5 to 10 µm, preferably 1 to 6 µm, particularly preferably 1.5 to 5 µm auf. Preferably at least 50%, preferably at least 60%, particularly preferably at least 70% of the particles of active substance have a particle size which is within the size ranges mentioned above. Particularly preferably at least 80%, most preferably at least 90% of the particles of active substance have a particle size which is within the size ranges mentioned above.

In another aspect the present invention relates to suspensions which contain only one of the two active substances according to the invention without any other additives.

The suspensions according to the invention may be prepared using methods known in the art. For this, the constituents of the formulation are mixed with the propellent gas or gases (optionally at low temperatures) and filled into suitable containers.

The above-mentioned propellant-containing suspensions according to the invention may be administered using inhalers known in the art (pMDIs=pressurized metered dose inhalers). Accordingly, in another aspect, the present invention relates to pharmaceutical compositions in the form of suspensions as hereinbefore described combined with one or more inhalers suitable for administering these suspensions. Moreover the present invention relates to inhalers, characterised in that they contain the propellant-containing suspensions according to the invention described hereinbefore.

The present invention also relates to containers (cartridges) which when fitted with a suitable valve can be used in a suitable inhaler and which contain one of the above-mentioned propellant-containing suspensions according to the invention. Suitable containers (cartridges) and processes for filling these cartridges with the propellant-containing suspensions according to the invention are known in the art.

In view of the pharmaceutical activity of tiotropium the present invention also relates to the use of the suspensions according to the invention for preparing a pharmaceutical composition for inhalation or nasal administration, preferably for preparing a pharmaceutical composition for inhalative or nasal treatment of diseases in which anticholinergics may develop a therapeutic benefit.

Particularly preferably the present invention also relates to the use of the suspensions according to the invention for preparing a pharmaceutical composition for the inhalative treatment of respiratory complaints, preferably asthma or COPD.

The Examples that follow serve to illustrate the present invention in more detail, by way of example, without restricting it to their contents.

B.2.1.2 Examples of Aerosol Suspension Formulations

Suspensions containing other ingredients in addition to active substance and propellant gas:

Formulation Example 20

| constituents | concentration [% w/w] |
| --- | --- |
| tiotropium iodide | 0.02 |
| isopropyl myristate | 0.30 |
| HFA-227 | 20.00 |
| HFA-134a | 79.68 |

Formulation Example 21

| constituents | concentration [% w/w] |
| --- | --- |
| tiotropium chloride | 0.04 |
| oleic acid | 0.005 |
| HFA-227 | 99.955 |

Formulation Example 22

| constituents | concentration [% w/w] |
| --- | --- |
| tiotropium iodide | 0.02 |
| oleic acid | 0.01 |
| HFA-227 | 60.00 |
| HFA-134a | 39.97 |

Formulation Example 23

| constituents | concentration [% w/w] |
| --- | --- |
| tiotropium iodide | 0.02 |
| isopropyl myristate | 1.00 |
| HFA-227 | 98.98 |

Formulation Example 24

| constituents | concentration [% w/w] |
|---|---|
| tiotropium chloride | 0.02 |
| Myvacet 9-45 | 0.3 |
| HFA-227 | 99.68 |

Formulation Example 25

| constituents | concentration [% w/w] |
|---|---|
| tiotropium chloride | 0.02 |
| Myvacet 9-45 | 0.1 |
| HFA-227 | 60.00 |
| HFA-134a | 39.88 |

Formulation Example 26

| constituents | concentration [% w/w] |
|---|---|
| tiotropium chloride | 0.04 |
| Polysorbate 80 | 0.04 |
| HFA-227 | 99.92 |

Formulation Example 27

| constituents | concentration [% w/w] |
|---|---|
| tiotropium iodide | 0.01 |
| Polysorbate 20 | 0.20 |
| HFA-227 | 99.78 |

Formulation Example 28

| constituents | concentration [% w/w] |
|---|---|
| tiotropium chloride | 0.04 |
| Myvacet 9-08 | 01.00 |
| HFA-227 | 98.96 |

Suspensions containing only active substance and propellent gas:

Formulation Example 29

| constituents | concentration [% w/w] |
|---|---|
| tiotropium iodide | 0.04 |
| HFA-227 | 80.00 |
| HFA-134a | 19.96 |

Formulation Example 30

| constituents | concentration [% w/w] |
|---|---|
| tiotropium iodide | 0.02 |
| HFA-227 | 60.00 |
| HFA-134a | 39.98 |

Formulation Example 31

| constituents | concentration [% w/w] |
|---|---|
| tiotropium iodide | 0.02 |
| HFA-227 | 99.98 |

Formulation Example 32

| constituents | concentration [% w/w] |
|---|---|
| tiotropium iodide | 0.02 |
| HFA-134a | 99.98 |

Formulation Example 33

| constituents | concentration [% w/w] |
|---|---|
| tiotropium chloride | 0.02 |
| HFA-227 | 99.98 |

Formulation Example 34

| constituents | concentration [% w/w] |
|---|---|
| tiotropium chloride | 0.02 |
| HFA-134a | 99.98 |

Formulation Example 35

| constituents | concentration [% w/w] |
| --- | --- |
| tiotropium chloride | 0.02 |
| HFA-227 | 20.00 |
| HFA-134a | 79.98 |

Formulation Example 36

| constituents | concentration [% w/w] |
| --- | --- |
| tiotropium chloride | 0.04 |
| HFA-227 | 40.00 |
| HFA-134a | 59.96 |

B.3. Propellent Gas-Free Inhalable Aerosols

The new tiotropium salts tiotropium chloride or tiotropium iodide may optionally also be administered in the form of propellant-free inhalable aerosols. For administering these propellant-free inhalable aerosols the new tiotropium salts tiotropium chloride or tiotropium iodide are prepared in the form of pharmaceutical solutions.

The solvent may be water on its own or a mixture of water and ethanol. The relative proportion of ethanol compared with water is not limited but the maximum is up to 70 percent by volume, more particularly up to 60 percent by volume and most preferably up to 30 percent by volume. The remainder of the volume is made up of water. The preferred solvent is water without the addition of ethanol.

The concentration of the new tiotropium salts tiotropium chloride or tiotropium iodide according to the invention based on the amount of tiotropium in the finished pharmaceutical preparation depends on the therapeutic effect desired. For the majority of complaints that respond to tiotropium the concentration of tiotropium is between 0.0005 and 5 wt. %, preferably between 0.001 and 3 wt. %.

The pH of the formulation according to the invention is between 2.0 and 4.5, preferably between 2.5 and 3.5 and more preferably between 2.7 and 3.3 and particularly preferably between 2.7 and 3.2. Most preferred are pH values with an upper limit of 3.1.

The pH is adjusted by the addition of pharmacologically acceptable acids. Examples of suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with the active substance. Of the organic acids, ascorbic acid, fumaric acid and citric acid are preferred. If desired, mixtures of the above acids may be used, particularly in the case of acids which have other properties in addition to their acidifying qualities, e.g. as flavourings or antioxidants, such as citric acid or ascorbic acid, for example. Hydrochloric acid is expressly mentioned as an inorganic acid.

Pharmacologically acceptable bases may also be used, if desired, for precisely titrating the pH. Suitable bases include for example alkali metal hydroxides and alkali metal carbonates. The preferred alkali metal ion is sodium. When such bases are used, care must be taken to ensure that the salts resulting from them which are then contained in the finished pharmaceutical formulation are also pharmacologically compatible with the above-mentioned acid.

According to the invention, the addition of editic acid (EDTA) or one of the known salts thereof, sodium edetate, as stabiliser or complexing agent is unnecessary in the present formulation.

Another embodiment contains editic acid and/or the above-mentioned salts thereof.

In a preferred embodiment the content based on sodium edetate is less than 10 mg/100 ml. In this case one preferred range is between 5 mg/100 ml and less than 10 mg/100 ml and another is between more than 0 and 5 mg/100 ml.

In another embodiment the content of sodium edetate is from 10 up to 30 mg/100 ml, and is preferably not more than 25 mg/100 ml.

In a preferred embodiment this additive is omitted altogether.

The remarks made above for sodium edetate also apply analogously to other comparable additives which have complexing properties and may be used instead of it, such as for example nitrilotriacetic acid and the salts thereof.

By complexing agents are preferably meant within the scope of the present invention molecules which are capable of entering into complex bonds. Preferably, these compounds should have the effect of complexing cations, most preferably metal cations.

In addition to ethanol, other co-solvents and/or other excipients may also be added to the formulation according to the invention.

Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters, provided that they are not also the solvent or suspension agent.

The terms excipients and additives in this context denote any pharmacologically acceptable and therapeutically beneficial substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as sorbitan trioleate, polyvinylpyrrolidone, other stabilisers, complexing agents, antioxidants and/or preservatives which prolong the shelf life of the finished pharmaceutical formulation, flavourings, vitamins and/or other additives known in the art. The additives also include pharmacologically acceptable salts such as sodium chloride.

The preferred excipients include antioxidants such as ascorbic acid, for example, provided that it has not already been used to adjust the pH, vitamin A, vitamin E, tocopherols and similar vitamins or provitamins occurring in the human body.

Preservatives may be used to protect the formulation from contamination with pathogens. Suitable preservatives are those which are known in the art, particularly benzalkonium chloride or benzoic acid or benzoates such as sodium benzoate in the concentration known from the prior art.

Preferred formulations contain, in addition to the solvent water and one of the new tiotropium salts, tiotropium chloride or tiotropium iodide, only benzalkonium chloride and sodium edetate. In another preferred embodiment, no sodium edetate is present.

The solutions according to the invention are preferably administered using the Respimat® inhaler. A more advance embodiment of this inhaler is disclosed in WO 97/12687 and FIG. 6 therein.

B.3.1. Examples of Propellant-Free Inhalable Aerosols

The Examples that follow serve to illustrate the present invention more fully by way of example without restricting it to their contents.

Formulation Example 37

| constituents | amount |
|---|---|
| tiotropium chloride | 0.03 g |
| benzalkonium chloride | 10 mg |
| sodium edetate | 10 mg |
| 1N HCl (aq) | ad pH 2.9 |
| water | ad 100 g |

Formulation Example 38

| constituents | amount |
|---|---|
| tiotropium chloride | 0.10 g |
| benzalkonium chloride | 10 mg |
| sodium edetate | 25 mg |
| 1N HCl (aq) | ad pH 3 |
| water | ad 100 g |

Formulation Example 39

| constituents | amount |
|---|---|
| tiotropium iodide | 0.05 g |
| benzalkonium chloride | 10 mg |
| sodium edetate | 10 mg |
| 1N HCl (aq) | ad pH 2.9 |
| water | ad 100 g |

Formulation Example 40

| constituents | amount |
|---|---|
| tiotropium iodide | 0.03 g |
| benzalkonium chloride | 10 mg |
| sodium edetate | 10 mg |
| 1N HCl (aq) | ad pH 2.9 |
| water | ad 100 g |

Formulation Example 41

| constituents | amount |
|---|---|
| tiotropium iodide | 0.10 g |
| benzalkonium chloride | 10 mg |
| sodium edetate | 25 mg |
| 1N HCl (aq) | ad pH 3 |
| water | ad 100 g |

Formulation Example 42

| constituents | amount |
|---|---|
| tiotropium chloride | 0.04 g |
| benzalkonium chloride | 10 mg |
| sodium edetate | 10 mg |
| 1N HCl (aq) | ad pH 2.9 |
| water | ad 100 g |

The invention claimed is:

1. A process for preparing tiotropium salts of formula 1 wherein $X^-$ denotes an anion other than $Y^-$, optionally in the form of solvates or hydrates thereof, selected from the group consisting of fluoride, chloride, bromide, iodide, $C_1$-$C_4$-alkylsulphate, sulphate, hydrogen sulphate, phosphate, hydrogen phosphate, dihydrogen phosphate, nitrate, maleate, acetate, trifluoroacetate, citrate, fumarate, tartrate, oxalate, succinate and benzoate, $C_1$-$C_4$-alkylsulphonate, which may optionally be mono-, di- or trisubstituted by fluorine at the alkyl group, or phenylsulphonate, which may optionally be mono- or polysubstituted by $C_1$-$C_4$-alkyl at the phenyl ring, comprising reacting a tiotropium salt of formula 2 wherein
Y⁻ denotes an anion other than X⁻, selected from the group consisting of halide, $C_1$-$C_{10}$-alkyl sulphonate, $C_1$-$C_{10}$-alkyl sulphate, $C_6$-$C_{10}$-aryl sulphonate, optionally in the form of solvates or hydrates thereof,
in a suitable solvent with an ion source Kat-X wherein Kat denotes a cation and X has the same definition as X⁻ above, and wherein the cation Kat of compounds Kat-X is selected from alkali or alkaline earth metals, ammonium ($NH_4^+$) or tetralkylammonium ($N(C_1$-$C_8$-alkyl$)_4^+$.

2. A process for preparing tiotropium salts of formula 1 wherein X⁻ denotes an anion other than Y⁻, optionally in the form of solvates or hydrates thereof, selected from the group consisting of fluoride, chloride, bromide, iodide, $C_1$-$C_4$-alkylsulphate, sulphate, hydrogen sulphate, phosphate, hydrogen phosphate, dihydrogen phosphate, nitrate, maleate, acetate, trifluoroacetate, citrate, fumarate, tartrate, oxalate, succinate and benzoate, $C_1$-$C_4$-alkylsulphonate, which may optionally be mono-, di- or trisubstituted by fluorine at the alkyl group, or phenylsulphonate, which may optionally be mono- or polysubstituted by $C_1$-$C_4$-alkyl at the phenyl ring, comprising reacting a tiotropium salt of formula 2 wherein
Y⁻ denotes an anion other than X⁻, selected from the group consisting of halide, $C_1$-$C_{10}$-alkyl sulphonate, $C_1$-$C_{10}$-alkyl sulphate, $C_6$-$C_{10}$-aryl sulphonate, optionally in the form of solvates or hydrates thereof,
in a suitable solvent with an ion source Kat-X wherein Kat denotes a cation and X has the same definition as X⁻ above, and, wherein the cation Kat of compounds of Kat-X is tetraalkylammonium ($N(C_1$-$C_8$-alkyl$)_4^+$.

* * * * *

UNITED STATES PATENT AND TRADEMARK OFFICE
CERTIFICATE OF CORRECTION

PATENT NO. : 8,686,148 B2  
APPLICATION NO. : 10/977753  
DATED : April 1, 2014  
INVENTOR(S) : Banholzer et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 657 days.

Signed and Sealed this
First Day of September, 2015

Michelle K. Lee
*Director of the United States Patent and Trademark Office*